United States Patent [19]

Simecek et al.

[11] Patent Number: 5,024,233
[45] Date of Patent: Jun. 18, 1991

[54] APPARATUS FOR DISTRIBUTION EVALUATION OF REGIONAL LUNG VENTILATION

[75] Inventors: Cyril Simecek, Pilsen; Jiri Ryba, Merklin, both of Czechoslovakia

[73] Assignee: TESLA, koncernovy podnik, Prague, Czechoslovakia

[21] Appl. No.: 598,805

[22] Filed: Apr. 10, 1984

Related U.S. Application Data

[63] Continuation-in-part of Ser. No. 356,324, Mar. 10, 1982, abandoned.

[30] Foreign Application Priority Data

Mar. 13, 1981 [CS] Czechoslovakia ............. 1836-81

[51] Int. Cl.⁵ ............................................. A61B 5/08
[52] U.S. Cl. ..................................... 128/659; 128/725
[58] Field of Search ..................... 128/653, 659, 725

[56] References Cited

U.S. PATENT DOCUMENTS 3,344,275 9/1967 Marchal et al. ............... 128/653 X
3,947,689 3/1976 Wagner .............................. 378/151
4,289,968 9/1981 LeMoy ............................ 250/363 S

FOREIGN PATENT DOCUMENTS 0623278 5/1979 U.S.S.R. ............................. 128/654

OTHER PUBLICATIONS

Bell, R. L. et al., "Enhanced Scintigraphic Information Display Using Computer-Generated Ratio Techniques", Jrnl. Nucl. Med. V11 #11 Nov. 1970.

Primary Examiner—Francis Jaworski
Attorney, Agent, or Firm—Klein & Vibber

[57] ABSTRACT

Distribution evaluation of regional lung ventilation is obtained by placing a radionuclide and an array of scintillation detectors on opposite sides of a subject from evaluation units. Each of the signals from evaluation units of the detectors is stored in a memory. The signals are compared in a comparison block, and the comparison is recorded by a recorder.

3 Claims, 2 Drawing Sheets 5,024,233

APPARATUS FOR DISTRIBUTION EVALUATION OF REGIONAL LUNG VENTILATION

This application is a continuation-in-part of application Ser. No. 356,324, filed Mar. 10, 1982 now abandoned.

BACKGROUND OF THE INVENTION

The present invention relates to apparatus for the distribution evaluation of regional lung ventilation by means of the absorption of radioactive radiation emitted by an enclosed radionuclide which after passing through the subject being measured, is sensed by a set of scintillation detectors.

At present, the nonuniform distribution of regional lung ventilation is most frequently judged from the prolonged mixing time, when breathing gaseous mixtures, while tracing the change in the concentration of a selected gas. In this case, the so-called wash-out or wash-in method can be employed. During tracing either nitrogen, inert gases, or radiopharmacons can be used. The methods employing the direct concentration measurement of nitrogen or inert gases, however, have a common disadvantage which consists in the fact that these methods are not sufficiently precise and therefore, can be used only for a general orientation. The location of the disorder is, however, impossible if these examinations are not carried out by gas sampling by means of gas analyzers corresponding to the gas used for the given purpose, the samples of the alveolar gas being taken from the bronchial tree. Another disadvantage of the examination of the regional function resides in the fact that the detected radiation of an isotope applied on the patient's body is also strongly influenced by the radiation absorption in the chest-wall and in the pleural effusion and so on, the magnitude of which cannot be designated, whereby the absolute and the relative evaluation of the regional ventilation is changed by a substantial fault making the result inaccurate.

The introduction of catheters is, however, unphysiological and pretentious for both the examining doctor and the patient. The application of radiopharmacons permits the localization of the changes to be determined, e.g. by means of a gamma camera. However, economically it is very pretentious and owing to the use of open radionuclides, it is possible only in special medical situations. The application of open radionuclides is also disadvantageous environmentally, and of the radiation loading of both the patient being examined and the examining physician. A certain contribution to remedying these insufficiencies of the methods mentioned above could be obtained from the application of the modified apparatus as described in the Czechoslovak Patent Specification, No. 196 123 (Simecek-Ryba: "The Apparatus for the Examinations of the Regional Lung Function"). By that apparatus regional ventilation can be registered but without the possibility of comparing and more exactly evaluating the changed distribution. The deficiency in that apparatus, however, can be seen in the fact that the number of the lung fields to be observed simultaneously is limited due to the low number of the available tracks of the lung fields to be observed simultaneously is limited due to the low number of the available tracks of the used recorder so that, in this case, the operations should be repeated during routine examinations. Owing to that, the accuracy of the evaluation has been considerably decreased with respect to the nonreproducibility of the conditions of the individual examinations following one another while simultaneously both the medical division and the patient being examined are exceedingly exposed to stress.

SUMMARY OF THE PRESENT INVENTION

The object of the present invention is to create apparatus for the distribution evaluation of regional lung ventilation by means of the absorption of radioactive radiation emitted by an enclosed radionuclide and after passing through the subject being measured, sensed by a set of scintillation detectors in which the output of every scintillation detector is connected to an associated input of an evaluation unit, the output of which is connected to an associated sector of a memory, and thereafter to a comparison block, the output of which is connected to a recorder in which both the comparison block and the memory are connected to a controlling unit.

It is a further object of the present invention to connect a spirometer to the associated sector of the memory and that the respective output of the memory is connected to the comparison block.

It is another object of the present invention that the output of the memory is on-line connected to a computer.

It is still a further object of the present invention to arrange a radiopaque stop between the radionuclide and the subject being measured and a control system of the radiopaque stop to be connected to the controlling unit.

It is still another object of the present invention to place the radionuclide into a collimator.

When compared to the devices which have been employed up to the present, the apparatus according to the present invention is more accurate and economically more advantageous.

Due to the fact that an enclosed radionuclide is employed, the application of this apparatus is not limited only to radioisotopic clinical divisions, and the radiation loading of the patient being examined and the attending personnel is relatively very low. When compared with the apparatus in which radiopharmacons are used, the apparatus according to the present invention is independent of the transport of the short half-life disintegration radioisotopes from the producer to the place of their future application so that thus any contamination of the environment can be prevented. The possibility of evaluating the regional distribution as well as the phase shifts of the regional breathing cycles is advantageous from the viewpoint of the diagnosis and the most efficient pharmacotherapy. The independence of the apparatus according to the present invention of employing the short half-life disintegration radioisotopes and a very low-degree radiation loading of the patient as well as the attending personnel permit repeated examinations to be carried out at any time, as required. The simultaneous tracing of both the regional lung ventilation and the spirometric curve permits the on-line converting of the relative values to the absolute ones.

Further details of the invention will now be explained with reference to the accompanying drawing showing the embodiments thereof.

DESCRIPTION OF THE INVENTION

Figure 1:
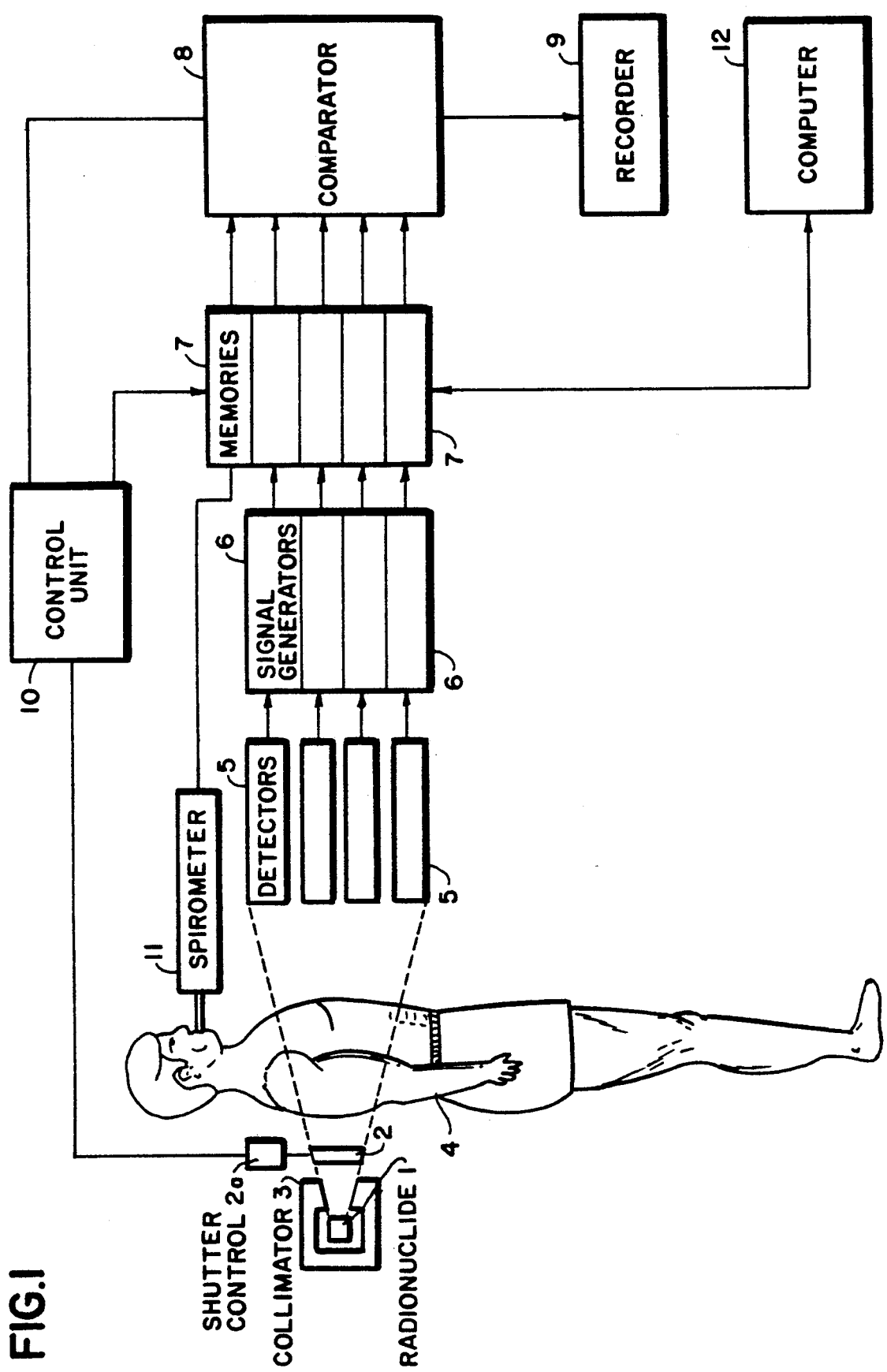
FIG. 1 is a general view of the apparatus of the present invention with a block diagram showing its circuitry.

A radionuclide 1 is located on one side of the subject 4 being examined while a set of the scintillation detectors 5 is placed on the opposite side of the subject 4. The output of every scintillation detector 5 is connected to the input of an associated evaluation unit 6 in which the electric signal of the scintillation detector 5 is processed and a signal suitable to be stored in a memory 7 is generated. The output of every evaluation unit 6 is connected to an associated sector of the memory 7. As a memory it is possible to employ, for example, a multitrack tape recorder for the recording of slowly variable analogue signals. The outputs of the individual sectors of the memory 7 are connected to a comparison block 8. The memory 7 and the comparison block 8 are connected to a controlling unit 10 which ensures a gradual evaluation of the records stored in the memory 7 through the comparison block 8 by a recorder 9 which is connected to the output of the comparison block 8. The on-line connection of both the memory 7 and a spirometer 11, which is connected to the memory 7, to a computer 12 permits the processing of the signals together with the converting of the relative values to the absolute ones and the display of the signals according to a preset program.

It is of an advantage to arrange a radiopaque stop 23 with a control system 2a between the radionuclide 1 and the subject 4 being measured. The control system 2a is used for opening the radiopaque stop 2 only during the radioactive exposure. The control system 2a of the radiopaque stop 2 is connected to the controlling unit 10. Further, the radionuclide 1 can be placed in a collimator 3 which collimates the radioactive radiation beam only within the required solid angle.

Figure 2:
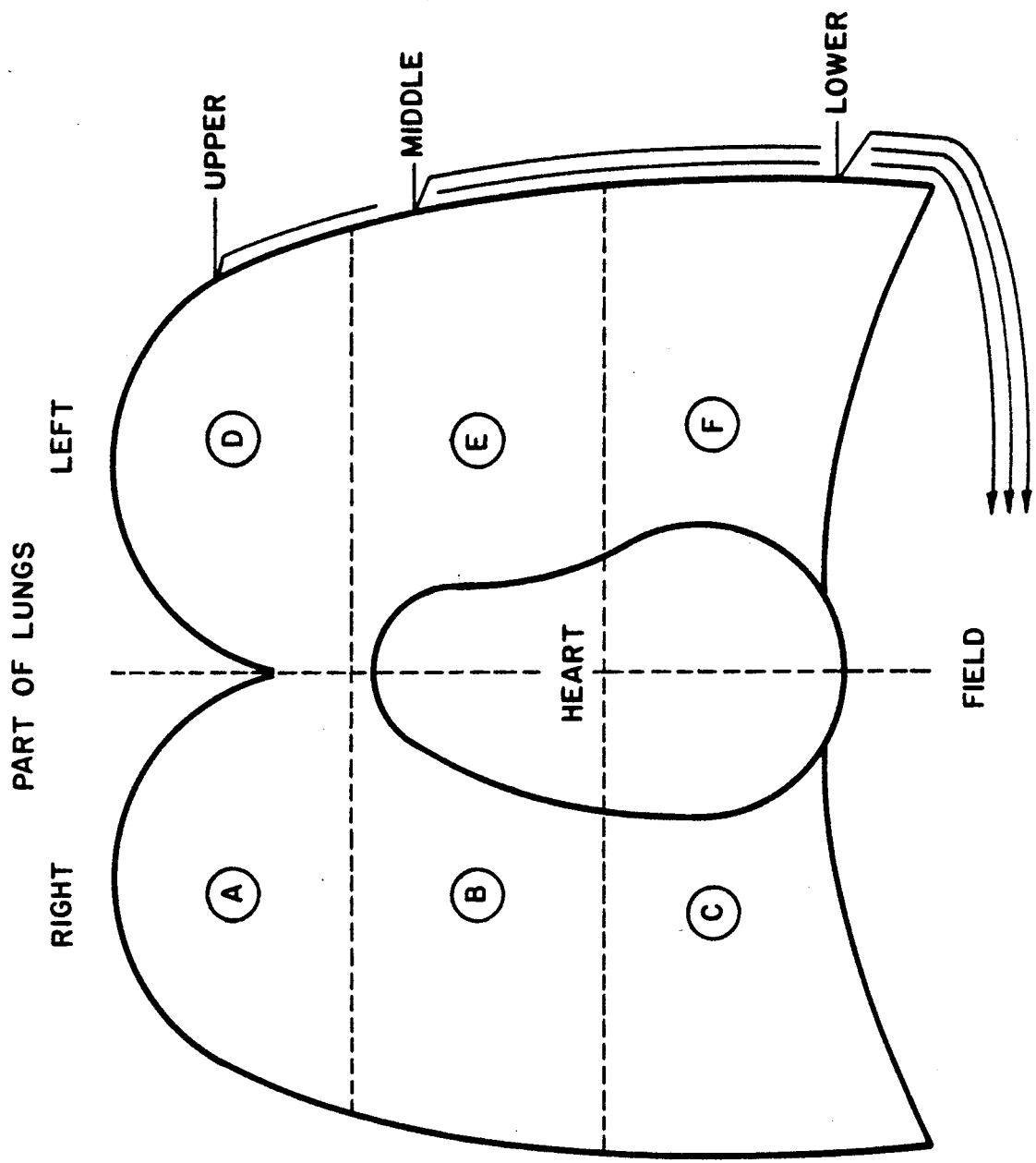
FIG. 2 is a schematic view of a patient's chest locating the position of the detectors relative to the various fields thereof.

The detectors are set in an array during examinations so that individual detectors evaluate the distribution in selected portions of the lung. As seen in FIG. 2, half of the detectors 5 are preferably spaced over the left lung and the second half over the right lung. When using six detectors, one pair of them is usually located at the upper fields of the lungs, the remaining two parts are placed at the middle and the low lung fields, respectively. During the breathing, the air contents of the lungs changes and the disturbed regional ventilation in each field of the lung results in changes of the absorbed radiation. By comparison of the changes in the quantity of the absorbed radiation as to the quantity and as to the time course, evaluation of the disturbed distribution of the ventilation of the quantity and time course can be carried out by mean of the computer or by means of a coordinate-recorded.

Although the invention is described and illustrated with reference to a single of embodiment thereof, it is to be expressly understood that it is in no way limited to the disclosure of such preferred embodiment but is capable of numerous modifications within the scope of the appended claims.

We claim:

1. Apparatus for the distribution evaluation of regional lung ventilation by means of the absorption of radioactive radiation comprising a radionuclide source of radiation fixedly mounted on one side of the subject being examined, and a plurality of scintillation detectors arranged on the opposite side of said subject in alignment with given fields of said lungs, respectively, for simultaneously sensing the passage of radiation through said subject, the outputs of said scintillation detectors being connected to an input of an associated evaluation unit, respectively, the output of each of said evaluation units being connected to the input of an associated sector of a memory, respectively, the output of each sector of said memory being connected to a comparison block, the output of said comparison block being connected to a recorder, said comparison block and said memory having further inputs connected to a controlling unit, thereby enabling successive comparison of the signals respectively associated with the given fields of said lungs, in which a spirometer is connected to an associated sector of the memory, and the respective output of the memory is connected to the comparison block.

2. The apparatus according to claim 1, in which a radiopaque stop is arranged between the radionuclide source and the subject being measured and a control system for the radiopaque stop is connected to the controlling unit.

3. The apparatus according to claim 1, 2, additionally comprising a collimator for containing said radionuclide source.

* * * * *